United States Patent
Iftekharuddin et al.

(10) Patent No.: US 8,632,186 B2
(45) Date of Patent: Jan. 21, 2014

(54) SYSTEMS, METHODS, AND COMPUTER-READABLE MEDIA FOR DETECTING AND PREDICTING A PROGRESSION OF RETINAL PATHOLOGIES

(71) Applicants: University of Memphis Research Foundation, Memphis, TN (US); Southern College of Optometry, Memphis, TN (US)

(72) Inventors: Khan M. Iftekharuddin, Virginia Beach, VA (US); Young June Kim, Shreveport, LA (US); Pinakin Gunvant Davey, Eastvale, CA (US)

(73) Assignees: University of Memphis Research Foundation, Memphis, TN (US); Southern College of Optometry, Memphis, TN (US)

( * ) Notice: Subject to any disclaimer, the term of this patent is extended or adjusted under 35 U.S.C. 154(b) by 0 days.

(21) Appl. No.: 13/633,814

(22) Filed: Oct. 2, 2012

(65) Prior Publication Data

US 2013/0114041 A1 May 9, 2013

Related U.S. Application Data

(63) Continuation of application No. 13/391,364, filed as application No. PCT/US2010/045902 on Aug. 18, 2010, now abandoned.

(60) Provisional application No. 61/234,803, filed on Aug. 18, 2009.

(51) Int. Cl.
*A61B 3/14* (2006.01)

(52) U.S. Cl.
USPC .......................................... 351/246; 351/203

(58) Field of Classification Search
USPC ..................................... 351/246, 203, 200, 205
See application file for complete search history.

(56) References Cited

U.S. PATENT DOCUMENTS

| 5,016,173 A | 5/1991 | Kenet et al. |
| 5,719,784 A * | 2/1998 | Clark et al. ..................... 702/28 |

(Continued)

OTHER PUBLICATIONS

International Preliminary Report on Patentability for International Application PCT/US2010/045902 mailed Feb. 21, 2012.

(Continued)

*Primary Examiner* — Hung Dang
(74) *Attorney, Agent, or Firm* — Edwards Wildman Palmer LLP; Peter F. Corless; Carolina E. Save

(57) ABSTRACT

One aspect of the invention provides a method for training a classification algorithm to detect a retinal pathology. The method includes: for a plurality of pseudo two-dimensional data sets of one-dimensional data points, each pseudo two-dimensional data point representing RNFL thickness values for a subject and corresponding index values for the data points: performing fractal analysis on the data set to calculate a plurality of fractal dimensions and calculating a plurality of slopes between each fractal dimension; combining the plurality of slopes for subjects labeled as pathologic into a pathologic data set; combining the plurality of slopes for subjects labeled as healthy into a healthy data set; and applying a linear discriminant function the pathologic data set and the healthy data set; thereby training a classification algorithm to detect the retinal pathology.

20 Claims, 14 Drawing Sheets

(56) References Cited

U.S. PATENT DOCUMENTS

| | | | |
|---|---|---|---|
| 5,815,242 A | | 9/1998 | Anderson et al. |
| 5,993,001 A | | 11/1999 | Bursell et al. |
| 6,364,486 B1 | * | 4/2002 | Ball et al. .................. 351/203 |
| 2004/0258310 A1 | * | 12/2004 | Giger et al. ................ 382/190 |
| 2006/0135867 A1 | * | 6/2006 | Essock et al. .............. 600/410 |
| 2007/0197932 A1 | * | 8/2007 | Feke et al. ................. 600/558 |

OTHER PUBLICATIONS

International Search Report on Patentability for International Application PCT/US2010/045902 mailed Mar. 3, 2011.

Written Opinion for International Application PCT/US2010/045902 mailed Mar. 3, 2011.

Essock et al., "Analysis of GDx-VCC polarimetry data by Wavelet-Fourier Analysis (WFA) across glaucoma stage," Invest Ophthal and Vis. Sci., 46(8):2838-2847 (2005).

Essock et al., "Fourier analysis of nerve fiber layer measurements from scanning laser polarimetry in glaucoma: emphasizing shape characteristics of the 'double-hump' pattern," J. Glaucoma, 9:444-452 (2000).

Gunvant et al., "Application of shape-based analysis methods to OCT retinal nerve fiber layer data in glaucoma," Journal of Glaucoma, 16:543-548 (2007).

Gunvant et al., "Predicting subsequent visual field loss in glaucomatous subjects with disc hemorrhage using RNFL polarimetry," J Glaucoma, 14-20-25 (2005).

Broch, "The GDxVCC™ Early answers and ongoing assessment for glaucoma," Carl Zeiss Meditec AG, (2004).

Iftekharuddin, Techniques in Fractal Analysis and Their Applications in Brain MRI, Medical Imaging Systems: Technology and Applications, vol. 1: Analysis and Computational Methods, World Scientific Publication, ISBN 981-256-993-6 (2005).

Iftekharuddin et al., "Automatic brain tumor detection in MRI: methodology and statistal validation," Proceedings of the SPIE Symposium and Medical Imaging, 5747:2012-2022 (2005).

Iftekharuddin et al., "Fractal-based Brain Tumor Detection in Multimodal MRI," Invited Paper for special issue on Emergent Applications of Fractals and Wavelets in Biology and Bio-medicine in Applied Mathematics and Computation, 207:23-42 (2000).

Medeiros et al., "Fourier analysis of scanning laser polarimetry measurements with variable corneal compensation in glaucoma," Invest Ophthalmol Vis Sci., 44:2606-2612 (2003).

Quigley et al., "Quantitative studies of retinal nerve fiber layer defects," Arch Ophthalmol, 100:807-814, (1982).

Pollicott, "Hausdorff Dimension and Asymptotic Cycles," Transactions of the American Mathematical Society, 355 (8):3241-3252 (2003).

Pearson, "On Lines and Planes of Closet Fit to Systems of Points in Space," Philosophical Magazine, 2:559-572 (1901).

Das, "Hausdorff Measures, Dimensions and Mutual Singularity," Transactions of the American Mathematical Society, 357(11):4249-4268 (2005).

* cited by examiner

SYSTEMS, METHODS, AND COMPUTER-READABLE MEDIA FOR DETECTING AND PREDICTING A PROGRESSION OF RETINAL PATHOLOGIES

CROSS-REFERENCE TO RELATED APPLICATIONS

This application is a continuation application of U.S. application Ser. No. 13/391,364 filed on Feb. 20, 2012, which is a national entry of International Application No. PCT/US2010/045902 having an international filing date of Aug. 18, 2010, which claims the benefit of U.S. Provisional Patent Application Ser. No. 61/234,803, filed Aug. 18, 2009. The entire contents of each application are hereby incorporated by reference herein.

BACKGROUND

As humans live longer, the occurrence and severity of retinal pathologies such as glaucoma, macular degeneration, macular edema, and the like continues to increase.

Glaucoma is an irreversible progressive optic neuropathy characterized by changes in the parapapillary retinal nerve fiber layer (RNFL) and optic disc. The human eye has about 0.75 to 1.25 million retinal ganglion cells that transmit the visual information from the eye to the brain. At a cellular level, glaucoma is characterized by a progressive death of these cells and their axons by a process of apoptosis that is measured as a progressive thinning of nerve fiber layer and neuroretinal rim tissue of the optic disc. The heterogeneous nature of the disease and redundancy in the visual system makes glaucoma very difficult to identify in early stages of the disease, thus making glaucoma the leading cause of blindness worldwide.

Macular degeneration is a medical condition that results in a lost of vision in the center of the visual field (the "macula") because of damage of the retina. In the "dry" form, macular degeneration is caused by the accumulation of cellular debris ("drusen") between the retina and the choroids. In the "wet" form, blood vessels grow up from the choroids behind the retina.

Macular edema is a medical condition that occurs when fluid and protein deposits collect on or under the macula and cause the macula to thicken and swell.

Structural damage, such as RNFL defects, is often observed and precedes functional damage. Medical devices, such as the scanning laser polarimeters (GDx devices), optical coherence tomographs (OCTs), and Heidelberg retina tomographs that measure the RNFL, may aid in early diagnosis of retinal pathologies such as glaucoma.

The current analysis is usually limited to the mean of RNFL at different locations around the parapillary retina at a given distance from the optic disc as a function of angle. Such thickness graph, also known as temporal, superior, nasal, inferior, temporal (TSNIT) graph of thickness for a ring around the retina, shows a general double-hump pattern of thickness due to the much greater number of ganglion cell axons entering the disc superiorly and inferiorly. Although the mean RNFL can discriminate groups of glaucomatous individuals from ocular healthy individuals, classification performance can be quite limited when using mean thickness for classification.

Due to this issue, the TSNIT features have been mathematically characterized and it is proven that shape-analysis methods like Fast Fourier Analysis (FFA) and Wavelet-Fourier Analysis (WFA) have better classification performances in differentiating between glaucomatous eyes and the healthy eyes.

Fast Fourier analysis (FFA) linearly breaks up the features into sinusoidal curves (i.e., into a set of sinusoids in which each sinusoid is a different scale, or frequency) and thus has a different number of humps across the TSNIT data set. Wavelet-Fourier analysis adopts a discrete wavelet transform (DWT), which is more suitable for analyzing discontinuities and abrupt changes contained in signals.

However, both FFA and WFA techniques yield only marginal improvements over standard methods. Accordingly, there is a need for systems, methods, and computer-readable media for detecting glaucoma and other retinal pathologies that outperform both currently technology and FFA and WFA analysis.

Likewise, detection of glaucomatous progression is critical in monitoring glaucoma patients and preventing irreversible vision loss. Although measuring visual field loss through standard automated perimetry (SAP) has been widely used in diagnosing glaucomatous progression, it has been shown that structural changes in the retinal nerve fiber layer may precede functional changes obtained by SAP. Glaucomatous progression is also known to be difficult to differentiate from test variability. Accordingly, there remains a need for systems, methods, and computer-readable media for predicting a progression of retinal pathologies such as glaucoma.

SUMMARY OF THE INVENTION

One aspect of the invention provides a method for training a classification algorithm to detect a retinal pathology. The method includes: for a plurality of pseudo two-dimensional data sets of one-dimensional data points, each pseudo two-dimensional data point representing RNFL thickness values for a subject and corresponding index values for the data points: performing fractal analysis on the data set to calculate a plurality of fractal dimensions and calculating a plurality of slopes between each fractal dimension; combining the plurality of slopes for subjects labeled as pathologic into a pathologic data set; combining the plurality of slopes for subjects labeled as healthy into a healthy data set; and applying a linear discriminant function the pathologic data set and the healthy data set; thereby training a classification algorithm to detect the retinal pathology.

This aspect can have a variety of embodiments. In some embodiments, each data set was previously labeled as pathologic or healthy. In other embodiments, the method includes labeling each data set as pathologic or healthy. Labeling can be performed by a human or a machine.

In some embodiments, the retinal pathology is selected from the group consisting of: glaucoma, macular degeneration, and macular edema.

The method can include: receiving a plurality of one-dimensional RNFL data sets of one-dimensional data points, each one-dimensional data point representing an RNFL thickness value for a subject and converting the plurality of one-dimensional RNFL data sets into the plurality of pseudo two-dimensional data points by associating each data point in each one-dimensional RNFL data set with the corresponding index value. The plurality of one-dimensional RNFL data sets can be generated by an imaging device. The imaging device can be selected from the group consisting of: a scanning laser polarimeter, an optical coherence tomograph, and a Heidelberg retina tomograph.

The fractal dimension can be calculated using a technique selected from the group consisting of: a box-counting technique and a fractional Brownian motion technique. The fractal dimension can be calculated using a plurality of the techniques.

The method can include applying principal components analysis to the pathologic data set and the healthy data set.

In some embodiments, the linear discriminant function is Fisher's linear discriminant function.

The method can include testing the classification algorithm against a test set.

Another aspect of the invention provides a computer-readable medium whose contents cause a computer to perform a method for training a classification algorithm to detect a retinal pathology. The method includes: for a plurality of pseudo two-dimensional data sets of one-dimensional data points, each pseudo two-dimensional data point representing RNFL thickness values for a subject and corresponding index values for the data points: performing fractal analysis on the data set to calculate a plurality of fractal dimensions and calculating a plurality of slopes between each fractal dimension; combining the plurality of slopes for subjects labeled as pathologic into a pathologic data set; combining the plurality of slopes for subjects labeled as healthy into a healthy data set; and applying a linear discriminant function the pathologic data set and the healthy data set; thereby training a classification algorithm to detect the retinal pathology.

Another aspect of the invention provides a method of detecting a retinal pathology in a subject. The method includes: performing fractal analysis on a pseudo two-dimensional RNFL data set for the subject to calculate a plurality of fractal dimensions; calculating a plurality of slopes between each fractal dimension; and applying a classification algorithm to the plurality of slopes; thereby detecting a retinal pathology in a subject.

This aspect can have a variety of embodiments. In one embodiment, the method includes: receiving a plurality of one-dimensional RNFL data sets of one-dimensional data points, each one-dimensional data point representing an RNFL thickness value for a subject; and converting the plurality of one-dimensional RNFL data sets into the plurality of pseudo two-dimensional data points by associating each data point in each one-dimensional RNFL data set with the corresponding index value.

The one-dimensional RNFL data set can be generated by an imaging device. The imaging device can be selected from the group consisting of: a scanning laser polarimeter, an optical coherence tomograph, and a Heidelberg retina tomograph.

The fractal dimension can be calculated using a technique selected from the group consisting of: a box-counting technique and a fractional Brownian motion technique. The fractal dimension can be calculated using a plurality of the techniques.

The classification algorithm can be trained according to the methods described herein.

The retinal pathology can be selected from the group consisting of: glaucoma, macular degeneration, and macular edema.

Another aspect of the invention provides a computer-readable medium whose contents cause a computer to perform a method of detecting a retinal pathology in a subject. The method includes: performing fractal analysis on a pseudo two-dimensional RNFL data set for the subject to calculate a plurality of fractal dimensions; calculating a plurality of slopes between each fractal dimension; and applying a classification algorithm to the plurality of slopes; thereby detecting a retinal pathology in a subject.

Still another aspect of the invention provides a system for detecting a retinal pathology. The system includes: an imaging device and a computing device. The computing device is configured to implement a method including: performing fractal analysis on a pseudo two-dimensional RNFL data set for the subject to calculate a plurality of fractal dimensions: calculating a plurality of slopes between each fractal dimension; and applying a classification algorithm to the plurality of slopes.

Yet another aspect of the invention provides a method of predicting progression of a retinal pathology. The method includes: for a plurality of pseudo two-dimensional data sets of one-dimensional data points, each pseudo two-dimensional data point representing RNFL thickness values for a subject and corresponding index values for the data points, applying a feature-based analysis on the data set; combining the results from the feature-based analysis for subjects labeled as progressing into a progressing data set; combining the results from the feature-based analysis for subjects labeled as non-progressing into a non-progressing data set; and applying a linear discriminant function to the progressing data set and the non-progressing data set, thereby training a classification algorithm to predicting progression of the retinal pathology.

This aspect of the invention can have a variety of embodiments. Each data set can be previously labeled as progressing or non-progressing. The method can include labeling each data set as progressing or non-progressing. Labeling can be performed by a human or a machine.

The retinal pathology can be selected from the group consisting of: glaucoma, macular degeneration, and macular edema.

The method can further include: receiving a plurality of one-dimensional RNFL data sets of one-dimensional data points, each one-dimensional data point representing an RNFL thickness value for a subject and converting the plurality of one-dimensional RNFL data sets into the plurality of pseudo two-dimensional data points by associating each data point in each one-dimensional RNFL data set with the corresponding index value. The plurality of one-dimensional RNFL data sets can be generated by an imaging device. The imaging device can be selected from the group consisting of: a scanning laser polarimeter, an optical coherence tomograph, and a Heidelberg retina tomograph.

The feature-based technique can be selected from the group consisting of: fractal analysis and fast Fourier analysis. Fractal analysis can be performed using a technique selected from the group consisting of: a box-counting technique and a fractional Brownian motion technique. Fractal analysis can be performed using a plurality of the techniques.

The method can further include applying principal components analysis to the progressing data set and the non-progressing data set.

The linear discriminant function can be Fisher's linear discriminant function.

The method can further include testing the classification algorithm against a test set.

Another aspect of the invention provides a method of predicting progression of a retinal pathology in a subject. The method includes: performing a feature-based analysis on a pseudo two-dimensional RNFL data set for the subject and applying a classification algorithm to the results of the feature-based analysis, thereby detecting predicting progression of a retinal pathology in a subject.

This aspect can have a variety of embodiments. The method can include: receiving a plurality of one-dimensional RNFL data sets of one-dimensional data points, each one-dimensional data point representing an RNFL thickness value for a subject, and converting the plurality of one-dimensional RNFL data sets into the plurality of pseudo two-dimensional data points by associating each data point in each one-dimensional RNFL data set with the corresponding index value. The one-dimensional RNFL data set is generated by an imaging device. The imaging device can be selected from the group consisting of: a scanning laser polarimeter, an optical coherence tomograph, and a Heidelberg retina tomograph.

The feature-based technique can be selected from the group consisting of: fractal analysis and fast Fourier analysis. Fractal analysis can be performed using a technique selected from the group consisting of: a box-counting technique and a fractional Brownian motion technique. Fractal analysis can be performed using a plurality of the techniques.

The classification algorithm can be trained according to the methods described herein.

The retinal pathology can be selected from the group consisting of: glaucoma, macular degeneration, and macular edema.

Another aspect of the invention provides a computer-readable medium whose contents cause a computer to perform a method of predicting progression of a retinal pathology in a subject. The method includes: performing a feature-based analysis on a pseudo two-dimensional RNFL data set for the subject and applying a classification algorithm to the results of the feature-based analysis, thereby detecting predicting progression of a retinal pathology in a subject.

Yet another aspect of the invention provides a system for detecting a retinal pathology. The system includes: an imaging device and a computing device configured to implement a method including: performing a feature-based analysis on a pseudo two-dimensional RNFL data set for the subject to calculate a plurality of fractal dimensions and applying a classification algorithm to the results of the feature-based analysis.

FIGURES

For a fuller understanding of the nature and desired objects of the present invention, reference is made to the following detailed description taken in conjunction with the figure wherein.

Figure 10:
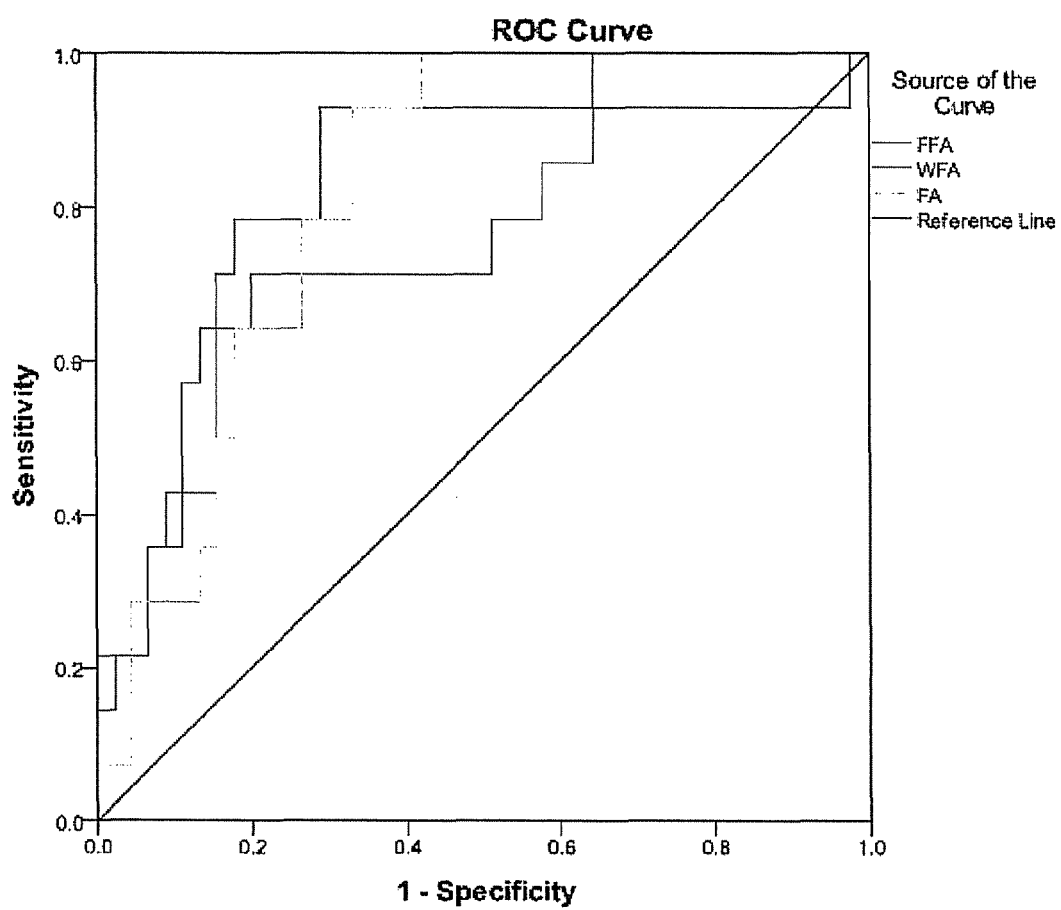
Figure 11:
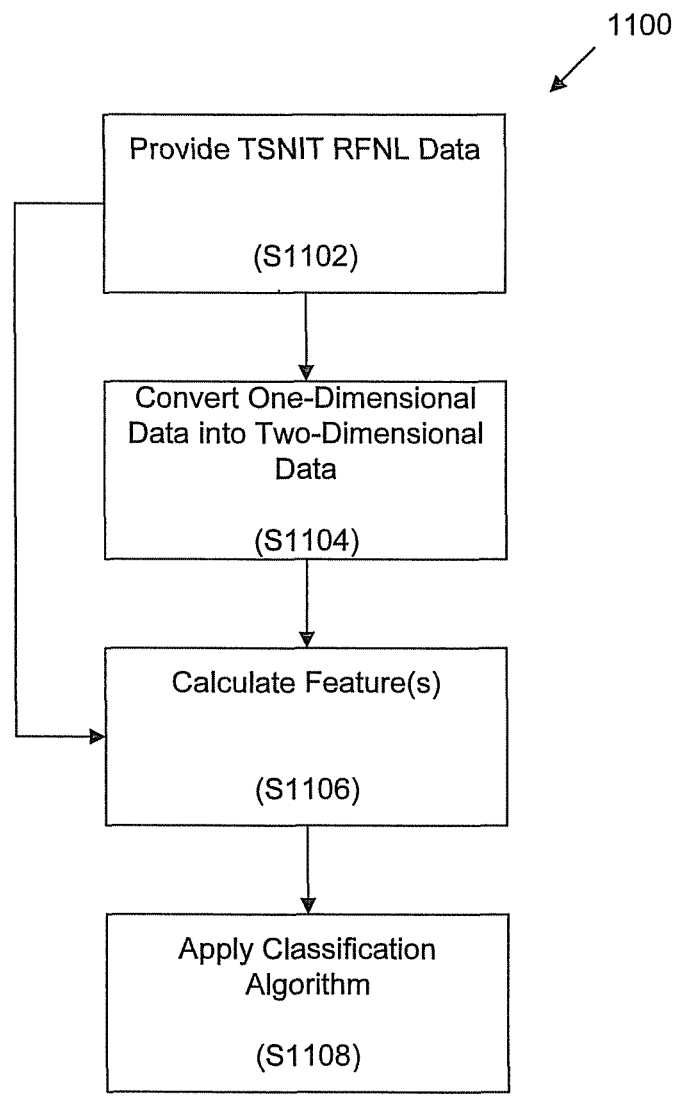

FIG. 10 provides a comparison of ROC curves for fast Fourier analysis (FFA), wavelet-Fourier analysis (WFA), and fractal analysis for the classification of progressors vs. non-progressors; and FIG. 11 provides a method 1100 of detecting and/or predicting progression of retinal pathologies.

DEFINITIONS

The instant invention is most clearly understood with reference to the following definitions:

As used in the specification and claims, the singular form "a," "an," and "the" include plural references unless the context clearly dictates otherwise.

A "subject" shall be understood to include any mammal including, but not limited to, humans. The term "subject" specifically includes primates.

A "health care provider" shall be understood to mean any person providing medical care to a subject. Such persons include, but are not limited to, medical doctors (e.g., ophthalmologists, optometrists, and the like), physician's assistants, nurse practitioners (e.g., an Advanced Registered Nurse Practitioner (ARNP)), nurses, residents, interns, medical students, or the like. Although various licensure requirements may apply to one or more of the occupations listed above in various jurisdictions, the term health care provider is unencumbered for the purposes of this patent application.

DESCRIPTION OF THE INVENTION

Aspects of the invention provide systems and methods for detection of retinal pathologies. Exemplary retinal pathologies include glaucoma, macular degeneration, macular edema, and the like. In some embodiments, a retinal pathology is detected through the use of fractal analysis of one or more images of a subject.

Fractals and Fractal Analysis

A fractal is a rough or fragmented geometric shape with an infinite nesting of structure at all scales. Each part of a fractal is a reduced-size copy of the whole. Fractal objects can be found everywhere in nature such as clouds, mountain ranges, coastlines, vegetables, snow flakes, and bacteria. Some of the properties of fractals are self-similarity, chaos, and non-integer fractal dimension (FD).

The fractal dimension offers a quantitative measure of self-similarity and scaling. The FD characterizes an object with a dimensionality greater than its topological dimension such that a fractal curve has a dimension between a straight line and a plane ($1<FD<2$) while a fractal surface has a dimension between a plane and three-dimensional space ($2<FD<3$).

One of the techniques to estimate the fractal dimension is the box-counting method, which is counting the number of boxes having side length (r) needed to cover the surface of a fractal object and the number (N) of grid boxes occupied by one or more pixels of the image. The equation of FD is as follows:

$$FD = \lim_{r \to 0^+} \frac{\ln(\text{number of self} - \text{similar pieces}, N)}{\ln\left(\text{magnification factor}, \frac{1}{r}\right)} \quad (1)$$

Because TSNIT data is a representation of pseudo two-dimensional thickness of RNFL, embodiments of the invention convert the one-dimensional GDx-VCC vector data into a pseudo two-dimensional image using the index as the y-coordinate. Such pseudo two-dimensional image representation of TSNIT data is then amenable to box-counting FD analysis without losing any generality of the RNFL thickness values.

Methods of Training a Classification Algorithm to Detect Retinal Pathologies

Figure 1:
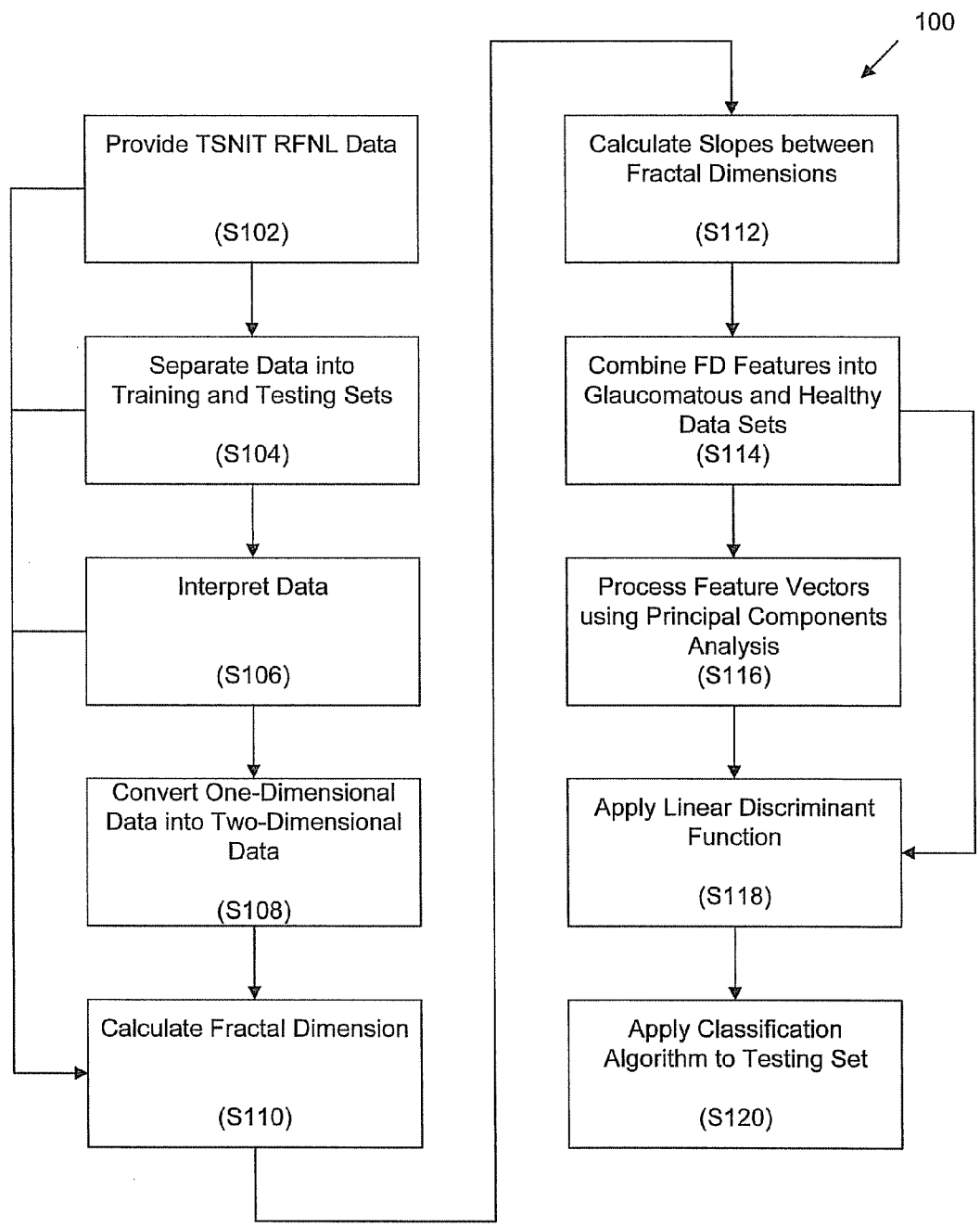
FIG. 1 depicts a method for training a classification algorithm to detect a retinal pathology in a subject according to one embodiment of the invention.

Referring now to FIG. 1, a method 100 is provided for training a classification algorithm to detect a retinal pathology in a subject.

In step S102, TSNIT RNFL data is provided. In some embodiments, the TSNIT RNFL data can be a one-dimensional data set consisting of data vectors obtained along a substantially circular path in the retina from a scanning laser polarimetry device such as the GDxVCC™ device available from Carl Zeiss Meditec Inc. of Dublin, Calif. In other embodiments, the TSNIT RNFL data is provided by an optical coherence tomograph and/or a Heidelberg retina tomograph.

In step S104, the data set is separated into a training set and a testing set. The training set is used to train the classification algorithm while the testing set is retained for testing the effectiveness of the trained classification algorithm. In some embodiments, a variation of 10-fold cross validation is used, as it is superior to split-half method and is especially advantageous when a very large sample is not available. For this procedure, the majority of subject data sets (in some embodiments, 90%) are selected for the training set, and the classification is applied to the small test set consisting of the remaining cases (10%).

In step S106, the one-dimensional data is interpreted to determine whether each subject is "pathologic" or "healthy." Interpretation can include manual interpretation by a qualified individual (e.g., a health care provider) or automated interpretation by one or more hardware or software devices.

Figure 2A:
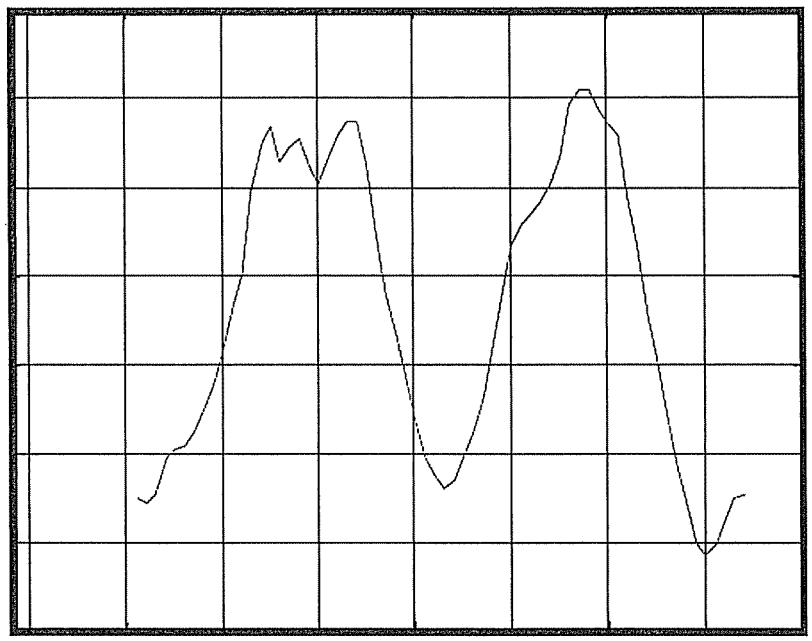
FIG. 2A depicts a plot of one-dimensional TSNIT RNFL vectors.
Figure 2B:
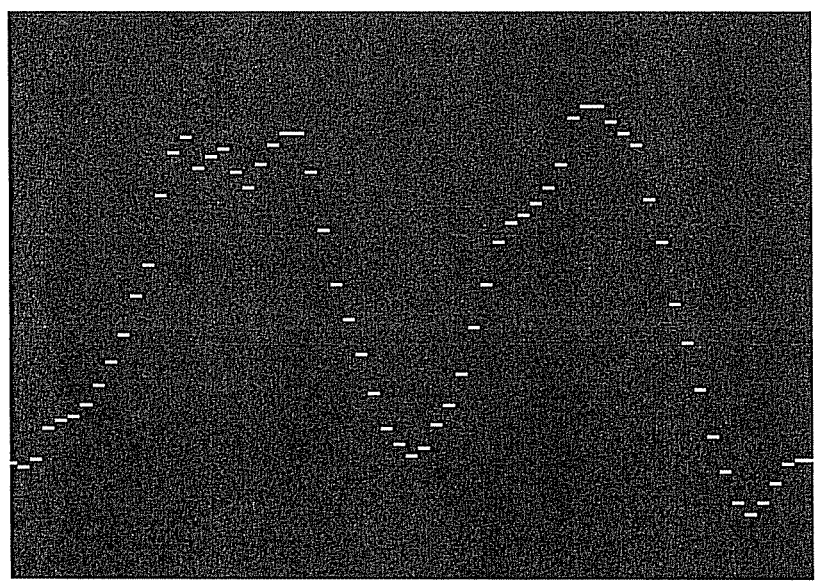
FIG. 2B depicts a plot of pseudo two-dimensional TSNIT data.

In step S108, the one-dimensional data is converted into a pseudo two-dimensional format by plotting each data point as the y-value with the corresponding index as the x-value. FIG. 2A depicts a plot of one-dimensional vectors and FIG. 2B depicts a pseudo two-dimensional image of a 64-point set of TSNIT features obtained using the GDxVCC™ device on a subject. In both FIGS. 2A and 2B, the y-axis represents RNFL thickness values and the x-axis represents the index of data points.

In step S110, fractal analysis is performed to calculate the Fractal Dimension (FD). In one embodiment, the FD can be calculated using the box-counting method on the pseudo two-dimensional RNFL data depicted in FIG. 2B for each subject. In another embodiment, the FD approximates the fractal dimension computation using the Hausdorff dimension, which can be calculated using the fractional Brownian motion techniques described herein or as described in publications such as Manav Das, "Hausdorff Measures, Dimensions, and Mutual Singularity," 357(11) Trans. Am. Math. Soc. 4249-68 (2005); Mark Pollicott, "Hausdorff Dimension & Asymptotic Cycles," 355(8) Trans. Am. Math. Soc. 3241-52 (2003); Jang-Mei Wu, "Hausdorff Dimension & Doubling Measures on Metric Spaces," 126(5) Trans. Am. Math. Soc. 1453-59 (1998).

Figure 3A:
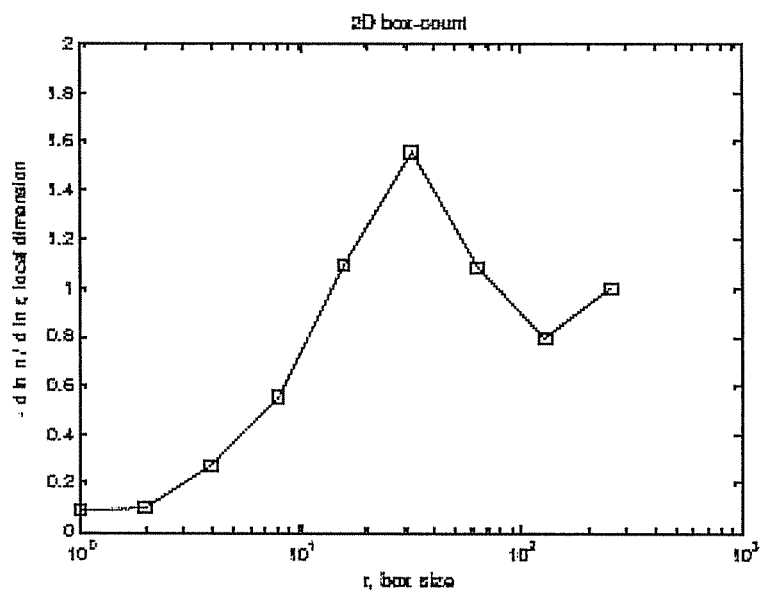
FIGS. 3A and 3B depict fractal dimension plots for two subjects.
Figure 3B:
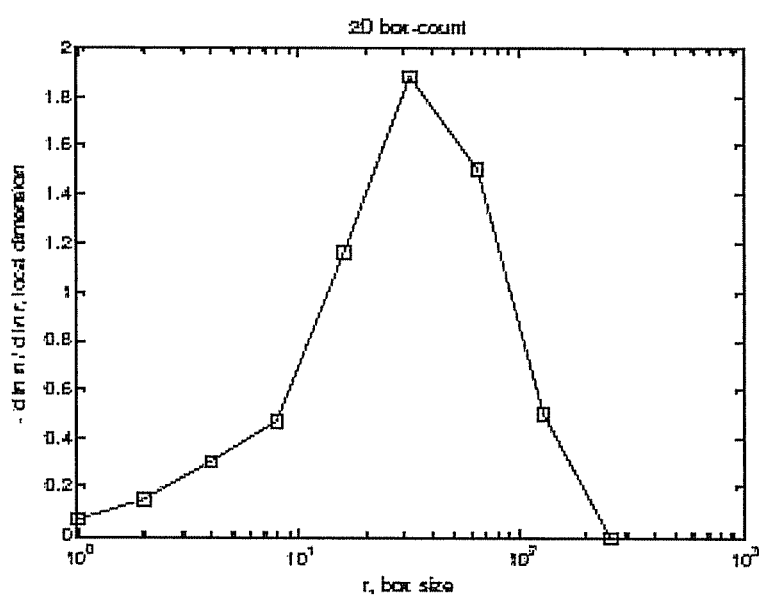

The resulting FD is piece-wise linear. In step S112, the slopes between each fractional dimension (e.g., box size) are extracted as new features. FIGS. 3A and 3B depict FD plots for two subjects. The plots show the fractal features for a single glaucomatous and healthy subject, respectfully. In each graph, the x-axis represents the size of the box for fractal computation and the y-axis represents the fractal dimension (FD) for each box size.

In step S114, the FD features for pathologic and healthy patients are each combined to produce pathologic and healthy data sets. In some embodiments, each data set is normalized.

In step S116, the feature vectors are further processed by using principal components analysis (PCA) to maximize the spread of the data points in the resultant multidimensional (reduced) feature space. PCA is described in a variety of publications such as I. T. Jolliffe, Principal Component Analysis (2d ed. 2002) and Karl Pearson, "On Line and Planes of Closest Fit to Systems of Points in Space," 2(6) Philosophical Magazine 559-72 (1901). The resultant lower dimensionality of the feature vectors can make the classifier more efficient and more stable.

In step S118, a linear discriminant function (LDF) such as Fisher's linear discriminant function is used to produce a classification algorithm of the reduced dimensionality FD data. The role of an LDF is to provide a criterion that optimally classifies a set of values into two categories (in the present study: pathologic eyes and healthy ones). Linear discriminant functions are described in publications such as Geoffrey J. McLachlan, Discriminant Analysis & Statistical Pattern Recognition (1992).

In some embodiments, the classification algorithm is tested on the testing set in step S120 to assure external validity of the classification algorithm. A variety of metrics can be used to assess the accuracy of the classification algorithm including area under receiver operating characteristics (AUROC), sensitivity, specificity, and the like.

FIRST WORKING EXAMPLE

Detection of Glaucoma

The method described herein was applied to detect glaucoma based on one-dimensional RNFL data obtained from a GDxVCC™ device available from Carl Zeiss Meditec Inc. of Dublin, California (utilizing software version 5.4.0.27). The data set included 111 ocular normal subjects and 116 glaucomatous subject (85 males and 142 female). Data was included for only one eye of each subject in the study. The mean age of ocular normal and glaucomatous subjects was 56.1 and 57.9 years respectively. The groups were matched for age and the difference in age between the ocular normal subjects and glaucomatous patients was not significant (independent samples t-test t=−1.08,p=0.28).

Figure 4A:
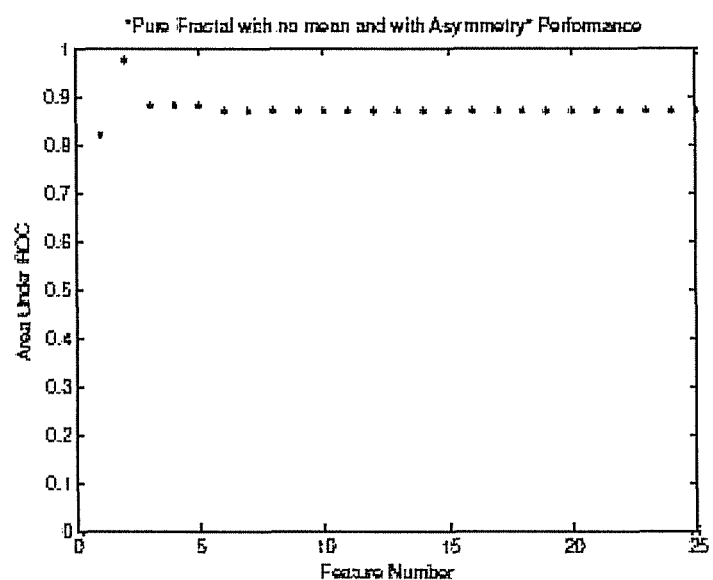
FIG. 4A depicts the area under receiver operating characteristic (AUROC) calculations for principal components analysis (PCA) features 1-25.

Referring now the FIG. 4A, AUROC is plotted for PCA features 1-25. As seen in FIG. 4A, only two PCA features are needed to achieve AUROC of 0.993.

Figure 4B:
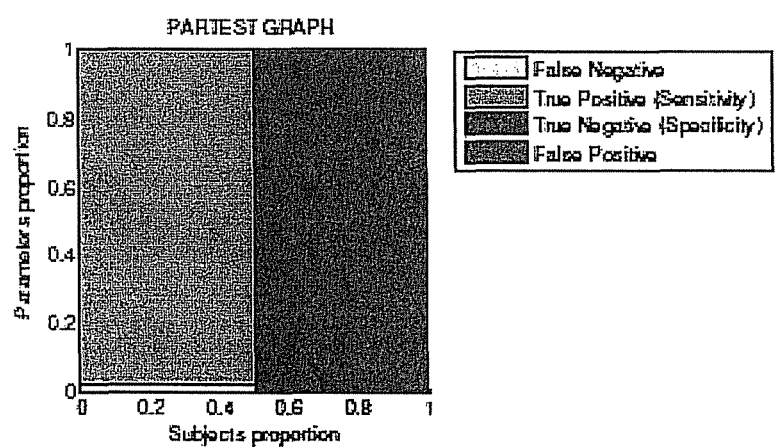
FIG. 4B depicts detection ability for classification algorithms trained according to one embodiment of the invention.

Referring now to FIG. 4B, shows the improved detection ability of the methods described herein. As depicted in FIG. 4B, the methods produce low levels of both false negatives and false positives.

Table 1 below shows that the AUROC improvement over the standard VCC methods (NFI) is largest and thus shows the significant advantage of using the methods herein for glaucoma detection.

TABLE 1

|  | FFA | WFA | NFI | Fractal |
|---|---|---|---|---|
| Sensitivity | 0.836 | 0.866 | 0.750 | 0.982 |
| Specificity | 0.821 | 0.791 | 0.856 | 0.995 |
| AUROC | 0.903 | 0.919 | 0.851 | 0.993 |

Detection and Prediction of Progression of Other Retinal Pathologies

In addition to the detection of glaucoma discussed herein, the methods described herein can be applied to detect other retinal pathologies such as macular degeneration and macular edema. Although the underlying physiology of such pathologies may differ from glaucoma, the classification algorithm is trained without knowledge of the physiology, and instead, is only concerned with a pattern presented in the data.

System for Detecting and/or Predicting a Progression of Retinal Pathologies

Figure 5:
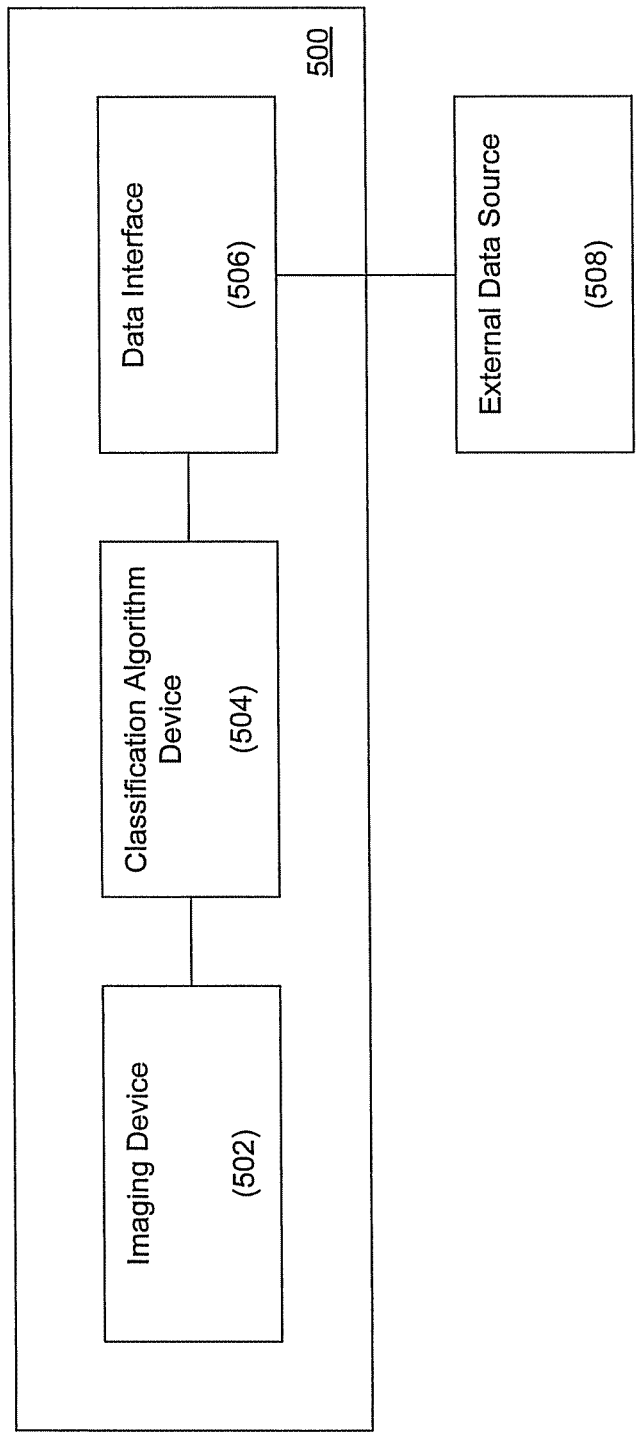
FIG. 5 depicts a retinal pathology detection and/or progression prediction system according to one embodiment of the invention.

Referring now to FIG. 5, a system 500 for detecting and/or predicting a progression of retinal pathologies is provided. The system includes an imaging device 502 and a device 504 for implementing one or more classification algorithms.

The imaging device 502 can be a variety of conventional ophthalmologic devices capable of imaging the RNFL such as scanning laser polarimeters (GDx devices) and optical coherence tomographs (OCTs), and/or a Heidelberg retina tomographs (HRTs).

The device 504 for implementing the classification algorithm(s) can be a variety of electronic devices capable of performing mathematical calculations. For example, a general purpose computer can be programmed to implement the methods described herein through software. Alternatively, the methods described herein can be encoded onto hardware and/or firmware devices.

In some embodiments, the system 500 includes a data interface 506 configured to communicate the output of the classification algorithm. A variety of devices can be used including optical devices (e.g., CRT displays, LCD displays, LED displays, printers, and the like) and audible devices (e.g., speakers and the like). Additionally or alternatively, data interface 506 can communicate the results to one or more external devices 508 such as a general purpose computer and/or a database. Such communication can be implemented through a variety of wired and wireless protocols.

In some embodiments, data interface 506 can include the appropriate hardware and/or software to implement one or more of the following communication protocols:

Universal Serial Bus (USB), USB 2.0, IEEE 1394, Peripheral Component Interconnect (PCI), Ethernet, Gigabit Ethernet, and the like. The USB and USB 2.0 standards are described in publications such as Andrew S. Tanenbaum, Structured Computer Organization § 3.6.4 (5th ed. 2006); and Andrew S. Tanenbaum, Modern Operating Systems 32 (2d ed. 2001). The IEEE 1394 standard is described in Andrew S. Tanenbaum, Modern Operating Systems 32 (2d ed. 2001). The PCI standard is described in Andrew S. Tanenbaum, Modern Operating Systems 31 (2d ed. 2001); Andrew S. Tanenbaum, Structured Computer Organization 91, 183-89 (4th ed. 1999). The Ethernet and Gigabit Ethernet standards are discussed in Andrew S. Tanenbaum, Computer Networks 17, 65-68, 271-92 (4th ed. 2003).

In other embodiments, data interface 506 can include the appropriate hardware and/or software to implement one or more of the following communication protocols: Bluetooth, IEEE 802.11, IEEE 802.15.4, and the like. The Bluetooth standard is discussed in Andrew S. Tanenbaum, Computer Networks 21, 310-17 (4th ed. 2003). The IEEE 802.11 standard is discussed in Andrew S. Tanenbaum, Computer Networks 292-302 (4th ed. 2003). The IEEE 802.15.4 standard is described in Yu-Kai Huang & Ai-Chan Pang, "A Comprehensive Study of Low-Power Operation in IEEE 802.15.4" in MSWiM'07 405-08 (2007).

In another embodiment, external data source 508 provides updated versions of the classification algorithms. For example, the manufacturer of the system 500 can periodically collect data sets (e.g., through interface 506) to further refine the classification algorithm and periodically "push" the updated algorithm to the systems 500 in individual health care provider offices.

Although components 502, 504, and 506 are depicted as individual components, one or more components can be combined to form a single device. Thus, the invention encompasses an imaging device that implements the classification algorithms described herein and includes a display for viewing the results of the classification algorithm.

Methods of Detecting Retinal Pathologies

Figure 6:
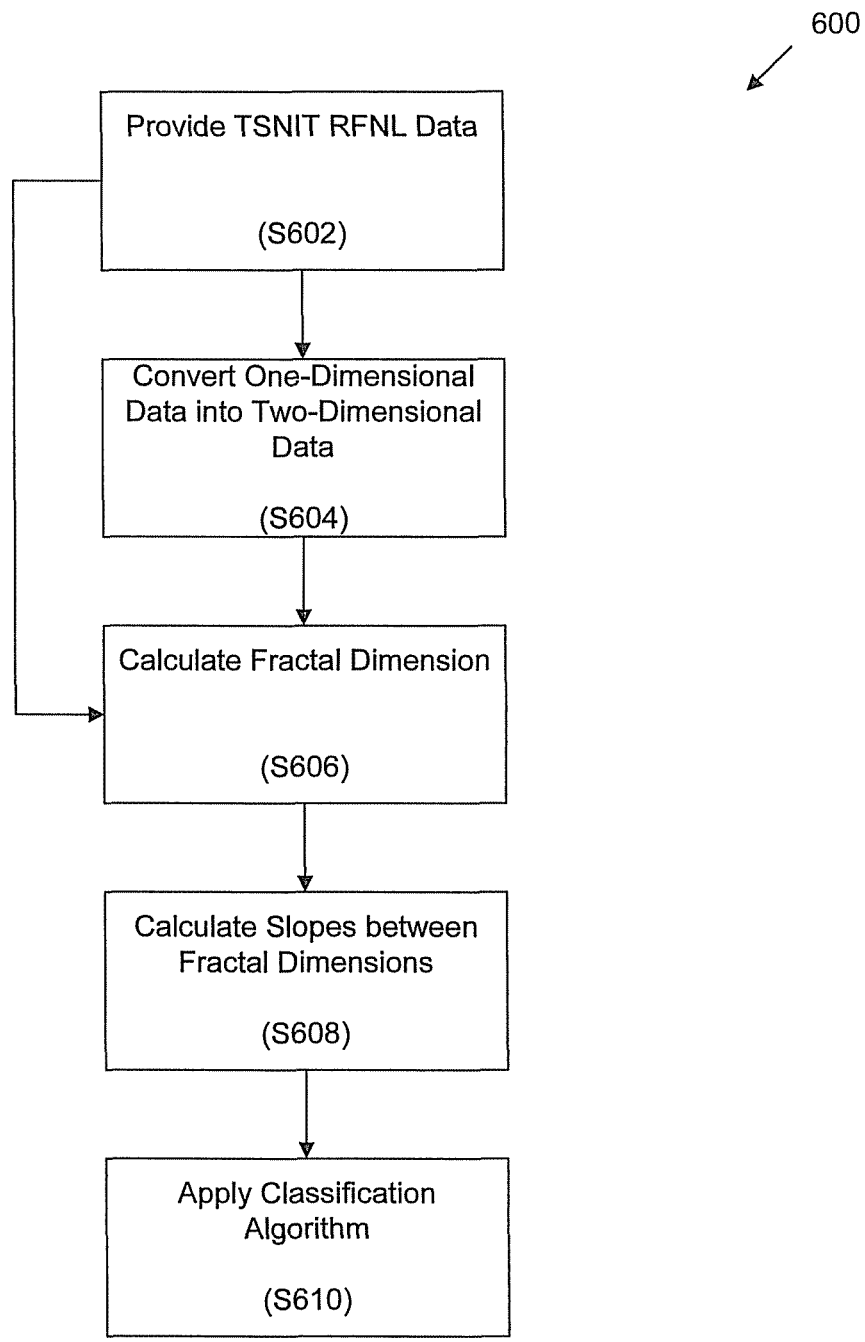
FIG. 6 depicts a method for detecting a retinal pathology in a subject according to one embodiment of the invention.

Referring now to FIG. 6, a method 600 of detecting retinal pathologies is provided. In step S602, TSNIT RNFL data is provided. In some embodiments, the TSNIT RNFL data is one-dimensional data. In such embodiments, the one-dimensional data is converted to pseudo two-dimensional data in step S604 as described herein. In other embodiments, the TSNIT RNFL data is pseudo two-dimensional data and the method proceed directly to step S606.

In step S606, the fractal dimension is calculated as discussed herein. In step S608, the slopes between the fractal dimensions are calculated as discussed herein. In step S610, a classification algorithm is applied to the fractal dimensions to determine whether the subject has a retinal pathology. The classification algorithm can be a classification algorithm trained in accordance with the description herein.

Further Methods Utilizing Optical Coherence Tomography Data

Figure 7A:
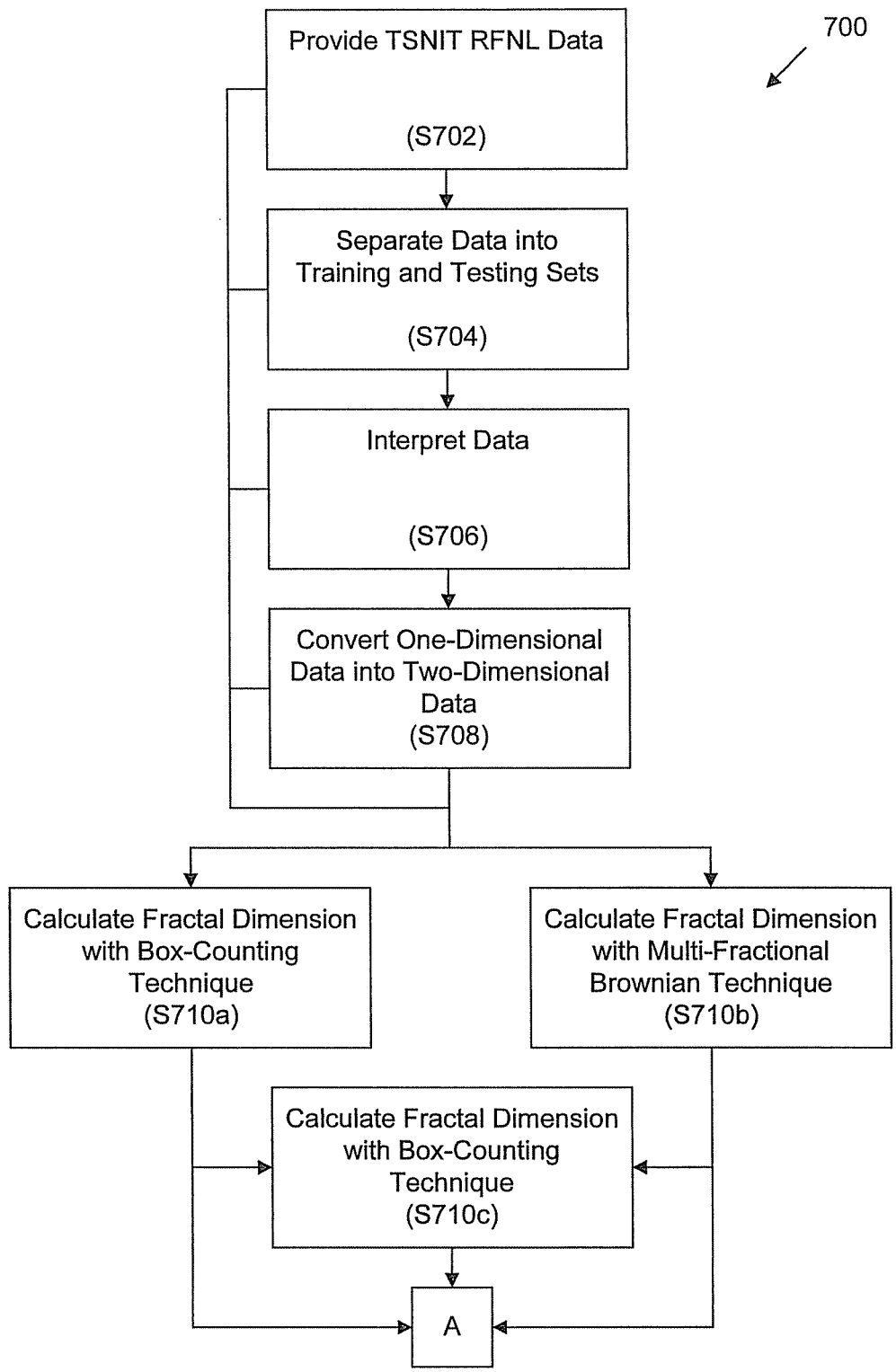
FIGS. 7A and 7B depict a further method of identifying a retinal pathology using multi-fractal features from optical coherence tomography.
Figure 7B:
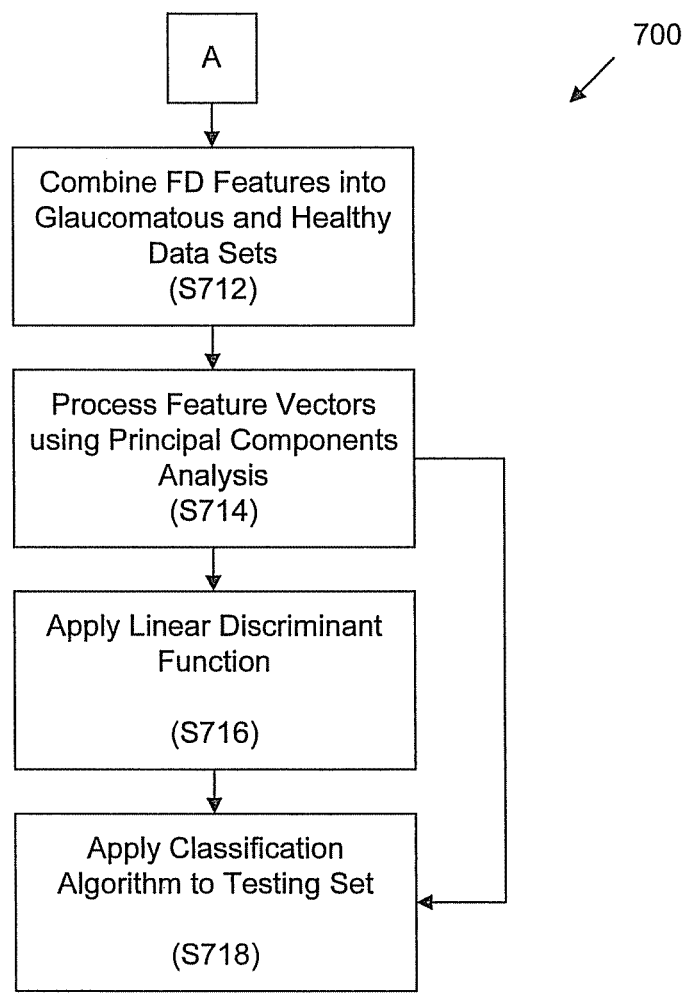

As discussed herein in the context of step S102, method 100 can be utilized in conjunction with optical coherence tomography data. Referring now to FIGS. 7A and 7B, further methods 700 of identifying a retinal pathology utilizing multi-fractal features from optical coherence tomography are provided.

In step S702, OCT RNFL data is provided. In some embodiments, the OCT RNFL data is obtained from optical coherence tomography device such as the STRATUS OCT™ available from Carl Zeiss Meditec, Inc. of Dublin, Calif.

In step S704, the data set are separated into a training set and a testing set. The training set is used to train the classification algorithm while the testing set is retained for testing the effectiveness of the trained classification algorithm. In some embodiments, a variation of 10-fold cross validation is used, as it is superior to the split-half method and is especially advantageous when a very large sample is not available. For this procedure, the majority of subject data sets (in some embodiments, 90%) are selected for the training set, and the classification is applied to the small test set consisting of the remaining cases (e.g., 10%).

In step S706, the one-dimensional data is interpreted to determine whether each subject is "pathologic" or "healthy." Interpretation can include manual interpretation by a qualified individual (e.g., a health care provider) or automated interpretation by one or more hardware or software devices.

OCT RNFL data is inherently 1D and, hence, may not be amenable for 2D fractal analysis using BC method. Accordingly, in step S708, the 1D OCT data can be converted into pseudo 2D format as follows. For each 1D RNFL thickness data set, its 1D maximum value (m) is calculated and rounded to the closest integer. Then, a 2D matrix is formed using the integers as the x-values and corresponding indices as the y-values. The resultant matrix is flipped and plotted to form the final pseudo-2D image.

In step S710, one or more techniques for calculating the fractal dimension (FD) can be utilized. Specifically, the fractal dimension can be calculated utilizing the box-counting technique (S710a) as discussed herein in the context of FIG. 1 and/or multi-fractional Brownian technique (S710b) as discussed below.

Referring still to step S710b, a fractional Brownian motion (fBm) model is a non-stationary and zero-mean Gaussian random model that well characterizes a random phenomenon. It is a random process based on self-affine fractal Brownian functions (fBfs).

The fBm is defined as $$B_H(t) - B_H(s) = \frac{1}{\Gamma(H+0.5)} \left\{ \int_{-\infty}^{0} [(t-s)^{H-0.5} - s^{H-0.5}] dB(s) \int_{-\infty}^{0} (t-s)^{H-0.5} dB(s) \right\} \quad (2)$$

where H is the Holder exponent, s and t are different observation times of the process, and $B_H$ is a generalization of Brownian motion.

The fractal dimension (FD) of an fBm is defined as $$FD_{fBm} = n + 1 - H \quad (3)$$

where n is the Euclidean dimension of the space.

Although fBm has proved to be useful in quantifying the random phenomenon such as tumor texture, fBm appears to be homogeneous or mono-fractal. It has been reported that there exist multi-fractal structure in real world signals such as tumor regions in MRI. Hence, multi-fractional Brownian motion (mBm) model may be more suitable for characterizing RNFL data.

The mBm is defined as $$x(at) = a^{H(t)} x(t) \quad (4)$$

where H(t) is the time varying scaling (or Holder) exponent, x(t) is a random process, and a is the scaling factor.

After a mathematical derivation, the expectation of the squared-magnitude of the wavelet transform $W_x$ of x(t) is $$\log(E[|W_x(a,t)|^2]) = (2H(t)+1)\log a + C \quad (5)$$

where C is a constant. Then, H(t) can be approximated as follows:

$$2H(t) = \lim_{a \to 0+} \frac{\log\left(\frac{1}{N}\sum_{i=0}^{N-1} |W_x(a,t)|^2\right)}{\log a} \quad (6)$$

Finally, the fractal dimension (FD) can be computed using Equation 3 as follows:

$$FD_{mBm} = n + 1 - H(t) \quad (7)$$

The main difference between the box-counting technique and the multi-fractional Brownian technique lies in the use of mono-fractals vs. multi-fractals. While the box-counting method (S710a) only calculates the homogenous mono-fractal, the mBm method calculates multi-fractals using wavelet filters.

Optionally in step S710c, the fractal dimensions obtained with the box-counting technique (S710a) are appended to the fractal dimensions obtained with the mBm technique (S710b). The combination of box-counting technique and the mBm technique can enhance the performance of the algorithm because the techniques may complement each other. The box-counting technique acquires its FD features by counting the occupied boxes and dividing them by the magnitude factor, which is the reciprocal of the size of the box. This technique is closely related to the morphology of the RNFL data (i.e., shape of the data). On the other hand, the mBm technique involves estimation of fractal characteristics in multi-resolution for non-stationary signals. Therefore, second technique may be complementary to the features that cannot be represented by the box-counting technique alone.

In step S712, the FD features for pathologic and healthy patients are each combined to produce pathologic and healthy data sets. In some embodiments, each data set is normalized.

In step S714, the feature vectors are further processed by using principal components analysis (PCA) to maximize the spread of the data points in the resultant multidimensional (reduced) feature space. The resultant lower dimensionality of the feature vectors can make the classifier more efficient and more stable.

In step S716, a linear discriminant function (LDF) such as Fisher's linear discriminant function is used to produce a classification algorithm of the reduced dimensionality FD data.

In some embodiments, the classification algorithm is tested on the testing set in step S718 to assure external validity of the classification algorithm. A variety of metrics can be used to assess the accuracy of the classification algorithm including area under receiver operating characteristics (AUROC), sensitivity, specificity, and the like.

SECOND WORKING EXAMPLE

Detection of Glaucoma with Optical Coherence Tomography

Standard ophthalmologic machine output is usually provided in terms of Superior Average, Inferior Average and Average Thickness of RNFL. The Inferior Average is the best at discriminating glaucoma from ocular normal individuals followed by Average Thickness and Superior Average with AUROC being 0.84, 0.76. and 0.70, respectively.

Figure 8A:
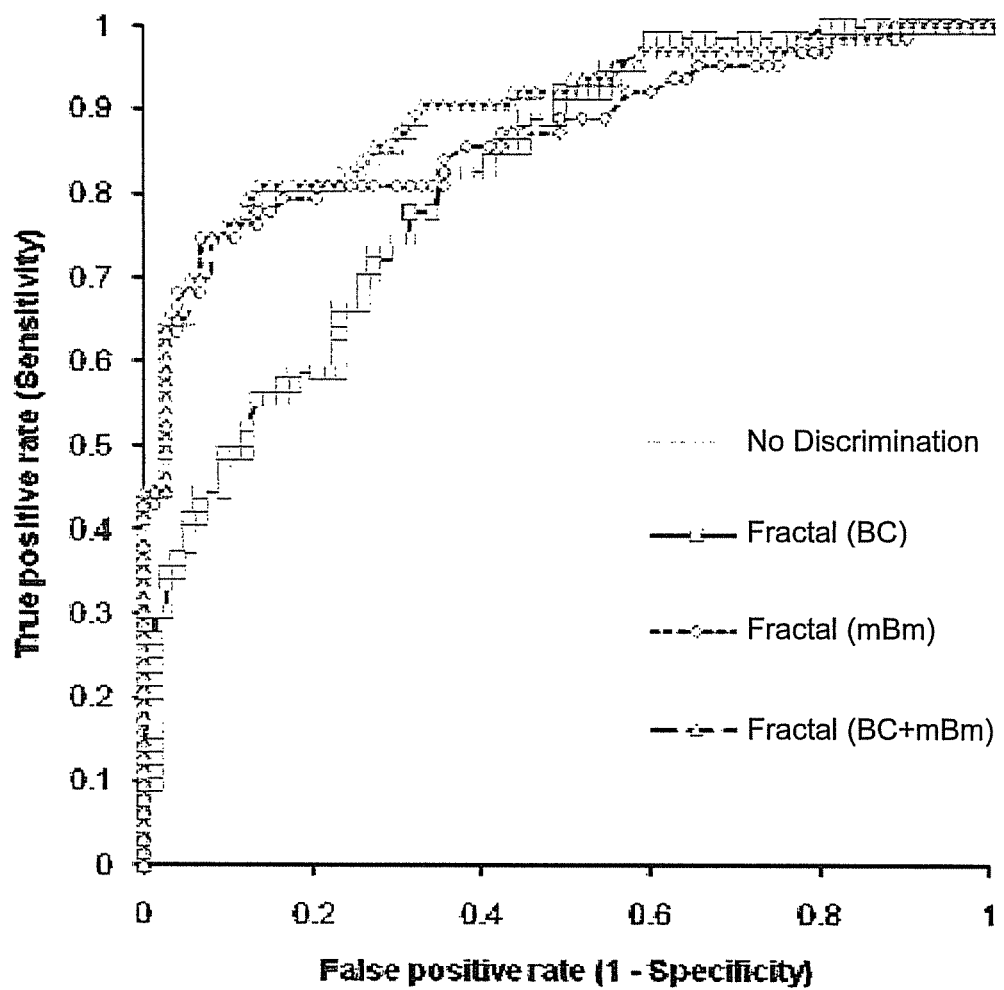
FIG. 8A depicts ROC curves for examples applications of the method of FIGS. 7A and 7B utilizing the box-counting, multi-fractional Brownian technique, and combined box-counting multi-fractional Brownian technique.
Figure 8B:
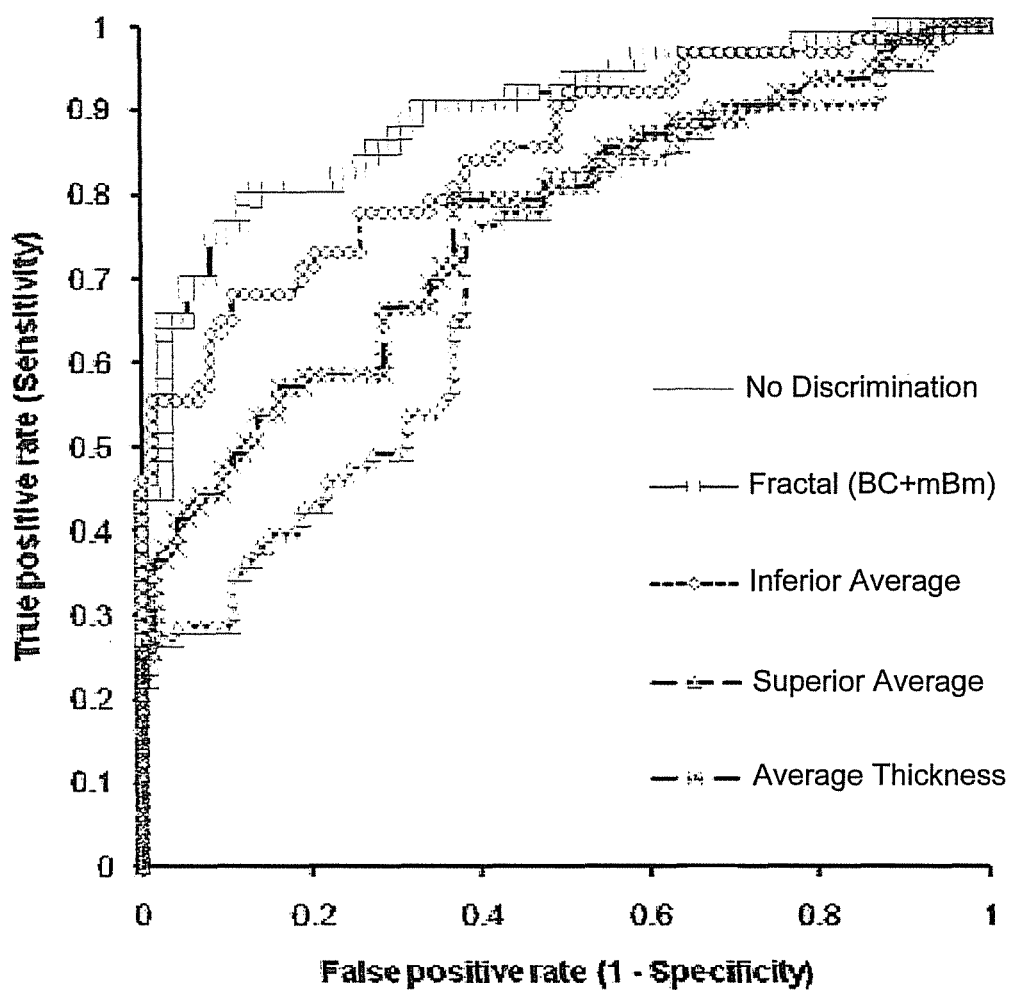
FIG. 8B depicts ROC curves for examples applications of the method of FIGS. 7A and 7B utilizing the box-counting, multi-fractional Brownian technique, and combined box-counting multi-fractional Brownian technique as well as for predictions based on Inferior Average, Superior Average, and Average Thickness measurements.

An experiment was conducted utilizing RNFL thickness data from 136 patients (63 with glaucoma and 73 having normal ocular function). FIGS. 8A and 8B show the comparison of ROC curves for these three measures. Note in FIG. 8A, the combined box-counting and mBm techniques perform the best among all three fractal-based techniques. (The corresponding AUROCs of box-counting, mBm, and the combined box-counting and mBm methods are 0.81, 0.87, and 0.89, respectively.

Comparison of the AUROCs of the best fractal-based technique and the set of standard machine measures shows that the diagnostic accuracy of the combined box-counting and mBm method is significantly greater than the Average Thickness and Superior Average by 13% and 19% respectively (p<0.0001 and p=0.001), whereas the difference in diagnostic accuracy of Inferior Average and the combined box-counting and mBm method was 5%, which was not statistically significant (p=0.058). (Comparisons were performed in accordance with the protocols of E. R. DeLong et al., "Comparing the areas under two or more correlated receiver operating characteristic curves: a nonparametric approach," 44 Biometrics 837-45 (1988). The summary of results is shown in Table 2.

TABLE 2

Comparison of AUROCs

|  | Average Thickness | Superior Average | Inferior Average | FA (BC) | FA (mBm) | FA (BC + mBm) |
|---|---|---|---|---|---|---|
| Sensitivity | 0.79 | 0.76 | 0.68 | 0.83 | 0.75 | 0.81 |
| Specificity | 0.63 | 0.60 | 0.89 | 0.64 | 0.93 | 0.86 |
| AUROC | 0.76 | 0.70 | 0.84 | 0.81 | 0.87 | 0.89 |

Methods of Predicting Progression of Retinal Pathologies

Figure 9A:
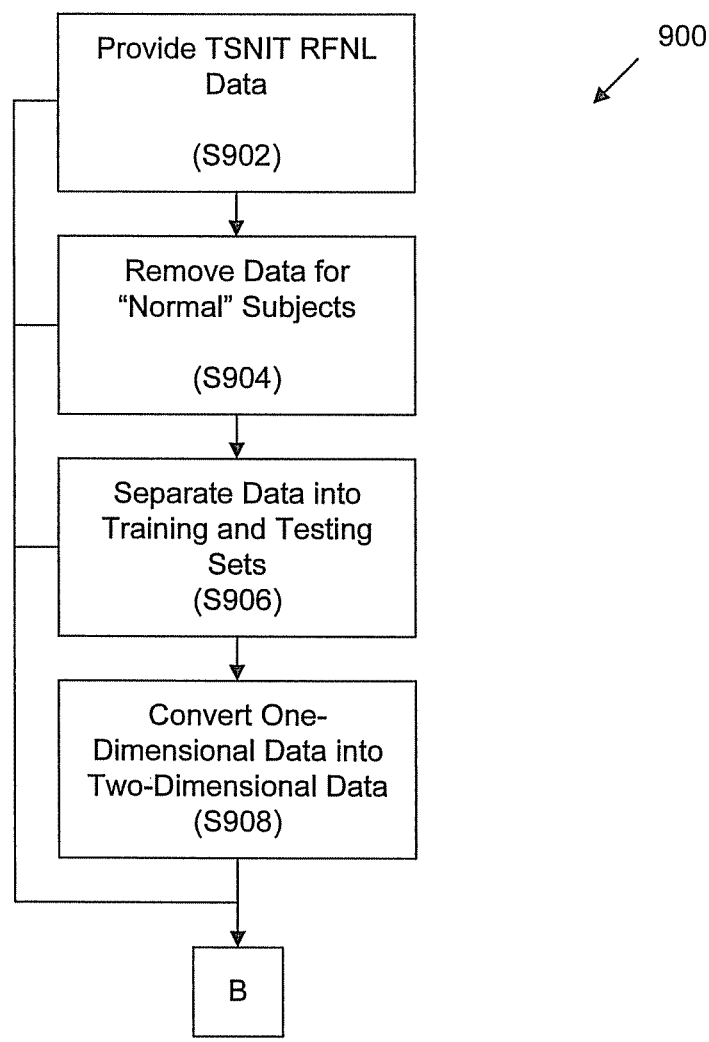
FIGS. 9A and 9B depict a method of predicting the progression of a retinal pathology.
Figure 9B:
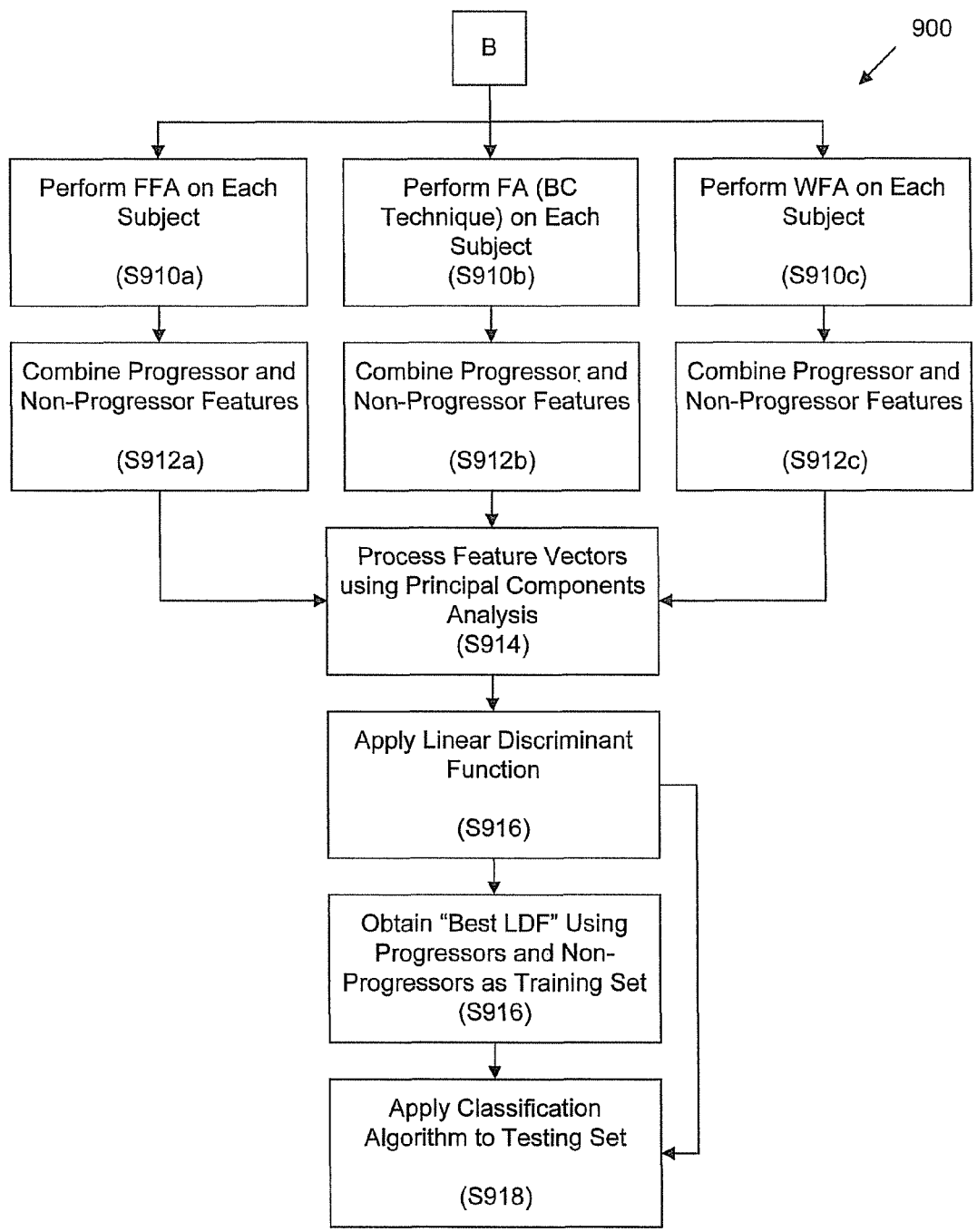

Referring now to FIGS. 9A and 9B, a method 900 of predicting the progression of a retinal pathology (e.g., glaucoma) is provided.

In step S902, TSNIT RNFL data is provided. In some embodiments, the TSNIT RNFL data can be a one-dimensional data set consisting of data vectors obtained along a substantially circular path in the retina from a scanning laser polarimetry device such as the GDxVCC™ device available from Carl Zeiss Meditec Inc. of Dublin, Calif. In other embodiments, the TSNIT RNFL data is provided by an optical coherence tomograph and/or a Heidelberg retina tomograph.

In step S904, any data for "normal" subjects (i.e., subjects that do not have glaucoma or another retinal pathology of interest) can be removed from the data set.

In step S906, the data set is separated into a training set and a testing set. The training set is used to train the classification algorithm while the testing set is retained for testing the effectiveness of the trained classification algorithm. In some embodiments, a variation of 10-fold cross validation is used, as it is superior to split-half method and is especially advantageous when a very large sample is not available. For this procedure, the majority of subject data sets (in some embodiments, 90%) are selected for the training set, and the classification is applied to the small test set consisting of the remaining cases (10%).

In step S908, the one-dimensional data is converted into a pseudo two-dimensional format by plotting each data point as the y-value with the corresponding index as the x-value as discussed herein.

In step S910, one or more feature-based techniques is applied to the in the training set. Examples of suitable feature-based techniques include fast Fourier analysis (FFA) (S910a), fractal analysis (e.g., box-counting fractal analysis) (S910b), wavelet-Fourier analysis (WFA) (S910c), and the like. Fast Fourier analysis and wavelet-Fourier analysis are described in publications such as E. A. Essock et al., "Fourier analysis of nerve fiber layer measurements from scanning laser polarimetry in glaucoma: emphasizing shape characteristics of the 'double-hump' pattern," 9 J. Glaucoma 444-52 (2000) and E. A. Es sock et al., "Analysis of GDx-VCC Polarimetry Data by Wavelet-Fourier Analysis across Glaucoma Stages," 46(8) Invest. Ophthalmol. & Vis. Sci. 2838-47 (August 2005).

In step S912, the features for progressors and non-progressors are each combined to produce progressor and non-progressor data sets. In some embodiments, each data set is normalized.

In step S914, the feature vectors are further processed by using principal components analysis (PCA) to maximize the spread of the data points in the resultant multidimensional (reduced) feature space.

In step S916, a linear discriminant function (LDF) such as Fisher's linear discriminant function is used to produce a classification algorithm of the reduced dimensionality FD data.

In step S918, the "best" linear discriminant function (LDF) is determined through use of the training set. In some embodiments, the "best" LDF can be the classifier that accounts for the maximum amount of variance.

THIRD WORKING EXAMPLE

Prediction of Progression of Glaucoma

An experiment was conducted with 96 patients, which were followed starting from the baseline up to 40 months. RNFL thickness was measured for each subject using the GDxVCC™ device approximately every six months. The subjects were deemed "progressors," "non-progressors," or "ocular healthy" on the basis of visual fields.

Case 1—Classification Between Progressors and Non-Progressor Patients (Training with Mixed Progressors and Non-progressors Patient Data)

The complete dataset comprised of baseline RNFL SLP data that includes 14 progressors and 45 non-progressors patients was utilized. Using 90% of this dataset, the target classifier for each feature-based analysis (i.e., FFA, WFA and FA) was obtained. This procedure found the representative features and by using LDA, the resulting LDF classifiers were obtained.

The classifiers that best characterize the progression of disease were selected next. The testing data was composed of the remaining 10% of the dataset. Here, the non-progressors were replaced with the average values of non-progressor at all visits to prevent over-fitting.

The best LDFs obtained from the training phase were next applied on the testing data. Each feature-based analysis was assessed by calculating AUROCs at 1 scan prior, 2 scans prior and 3 scans prior to the progression. The interval between successive scans (prior to progression) was approximately 6 months.

FIG. 10 provides a comparison of ROC curves for fast Fourier analysis (FFA), wavelet-Fourier analysis (WFA), and fractal analysis for the classification of progressors vs. non-progressors.

Table 3 below provides the AUROC values for fast Fourier analysis (FFA), wavelet-Fourier analysis (WFA), and fractal analysis by visit.

TABLE 3

AUROC Values for FFA, WFA, and FA Methods on Different Visits

| Method | AUROC (1 Scan Prior) | AUROC (2 Scan Prior) | AUROC (3 Scan Prior) |
|---|---|---|---|
| FFA | 0.82 | 0.71 | 0.63 |
| WFA | 0.78 | 0.78 | 0.67 |
| FA | 0.82 | 0.70 | 0.73 |

Case 1—Evaluation of Specificity in Ocular Healthy Patients

In this case, the training data and the classifiers (the best LDFs) remain the same as discussed in Case 1 for progressors and non-progressors case. However, the testing data is different and consists of 37 ocular normal patients. Here, only specificities can be obtained since the "progressors" patients are not included in testing. The purpose this testing is to assess the effectiveness of previous classifiers for avoiding false positives in ocular normal patients. The specificities of fast Fourier analysis (FFA), wavelet-Fourier analysis (WFA), and fractal analysis is depicted below in Table 4.

TABLE 4

Specificities for FFA, WFA, and FA LDFs

| Training/Testing | Specificity (FFA) | Specificity (WFA) | Specificity (FA) |
|---|---|---|---|
| Testing with the Best LDF Obtained in Case 1 for Glaucoma Prediction in Ocular Normal Patients | 0.86 | 0.76 | 0.86 |

Discussion

The statistical analysis above demonstrates that both fast Fourier analysis and fractal analysis feature-based analyses can predict glaucomatous progression with moderate accuracy. In addition, both FFA and FA methods can be useful in predicting progressive damage in ocular normal patients.

Further Methods of Detecting and Predicting Progression of Retinal Pathologies

Referring now to FIG. 11, a method 1100 of detecting and/or predicting progression of retinal pathologies is provided.

In step S1102, TSNIT RNFL data is provided. In some embodiments, the TSNIT RNFL data is one-dimensional data. In such embodiments, the one-dimensional data is converted to pseudo two-dimensional data in step S1104 as described herein. In other embodiments, the TSNIT RNFL data is pseudo two-dimensional data and the method proceed directly to step S1106.

In step S1106, the a feature-based analysis is performed as discussed herein. For example, fractal analysis (e.g., box-counting fractal analysis), fast Fourier analysis, and/or wavelet-Fourier analysis can be performed.

In step S1108, a classification algorithm is applied to the results of feature-based analysis to determine whether the subject has a retinal pathology and/or predict the progression of a retinal pathology. The classification algorithm can be a classification algorithm trained in accordance with the description herein.

INCORPORATION BY REFERENCE

All patents, published patent applications, and other references disclosed herein are hereby expressly incorporated by reference in their entireties by reference.

EQUIVALENTS

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A method for training a classification algorithm to detect a retinal pathology, the method comprising:
   for a plurality of pseudo two-dimensional data sets of one-dimensional data points, each pseudo two-dimensional data point representing RNFL thickness values for a subject and corresponding index values for the data points:
   performing fractal analysis on the data set to calculate a plurality of fractal dimensions; and
   calculating a plurality of slopes between each fractal dimension;
   combining the plurality of slopes for subjects labeled as pathologic into a pathologic data set;
   combining the plurality of slopes for subjects labeled as healthy into a healthy data set; and
   applying a linear discriminant function to the pathologic data set and the healthy data set;
   thereby training a classification algorithm to detect the retinal pathology.

2. The method of claim 1, wherein each data set was previously labeled as pathologic or healthy.

3. The method of claims 2, wherein labeling is performed by a human or a machine.

4. The method of claim 1, further comprising:
   labeling each data set as pathologic or healthy.

5. The method of claim 1, wherein the retinal pathology is selected from the group consisting of: glaucoma, macular ederma.

6. The method of claim 1, further comprising:
   receiving a plurality of one-dimensional RNFL data sets of one-dimensional data points, each one-dimensional data point representing an RNFL thickness value for a subject; and
   converting the plurality of one-dimensional RNFL data sets into the plurality of pseudo two-dimensional data points by associating each data point in each one-dimensional RNFL data set with the corresponding index value.

7. The method of claim 6, wherein the plurality of one-dimensional RNFL data sets are generated by an imaging device.

8. The method of claim 7, wherein the imaging device is selected from the group consisting of: a scanning laser polarimeter, an optical coherence tomograph, and a Heidelberg retina tomograph.

9. The method of claim 1, wherein the fractal dimension is calculated using a technique selected from the group consisting of: a box-counting technique and a fractional Brownian motion technique.

10. The method of claim 9, wherein the fractal dimension is calculated using a plurality of the techniques.

11. The method of claim 1, further comprising:
    applying principal components analysis to the pathologic data set and the healthy data set.

12. The method of claim 1, wherein the linear discriminant function is Fisher's linear discriminant function.

13. A computer-readable medium whose contents cause a computer to perform the method of claim 1.

14. A method of detecting a retinal pathology in a subject, the method comprising:
    performing fractal analysis on a pseudo two-dimensional RNFL data set for the subject to calculate a plurality of fractal dimensions;

calculating a plurality of slopes between each fractal dimension; and applying a classification algorithm to the plurality of slopes;

thereby detecting a retinal pathology in a subject.

15. A computer-readable medium whose contents cause a computer to perform a method of claim 14.

16. A system for detecting a retinal pathology, the system comprising:

an imaging device; and a computing device configured to implement the method of claim 14.

17. A method of predicting progression of a retinal pathology, the method comprising:

for a plurality of pseudo two-dimensional data sets of one-dimensional data points, each pseudo two-dimensional data point representing RNFL thickness values for a subject and corresponding index values for the data points, applying a feature-based analysis on the data set;

combining the results from the feature-based analysis for subjects labeled as progressing into a progressing data set;

combining the results from the feature-based analysis for subjects labeled as non-progressing into a non-progressing data set; and applying a linear discriminant function to the progressing data set and the non-progressing data set;

thereby training a classification algorithm to predicting progression of the retinal pathology.

18. A method of predicting progression of a retinal pathology in a subject, the method comprising:

performing a feature-based analysis on a pseudo two-dimensional RNFL data set for the subject; and applying a classification algorithm to the results of the feature-based analysis;

thereby detecting predicting progression of a retinal pathology in a subject.

19. A computer-readable medium whose contents cause a computer to perform a method of claim 18.

20. A system for detecting a retinal pathology, the system comprising:

an imaging device; and a computing device configured to implement the method of claim 19.

* * * * *